United States Patent [19]
Lajoie et al.

[11] Patent Number: 5,871,955
[45] Date of Patent: Feb. 16, 1999

[54] FIELD APPLICATION VECTORS

[75] Inventors: Curtis Lajoie, New Brunswick; Peter F. Strom, Highland Park, both of N.J.

[73] Assignee: Rutgers, The State University of New Jersey, New Brunswick, N.J.

[21] Appl. No.: 662,735

[22] Filed: Feb. 28, 1991

[51] Int. Cl.$^6$ .......................... C12P 21/02; C12N 15/63; C12N 15/78; C12N 9/00

[52] U.S. Cl. .................... 435/69.1; 435/71.1; 435/172.1; 435/183; 435/252.3; 435/252.34

[58] Field of Search .............................. 435/41, 42, 69.1, 435/71.1, 172.1, 183, 252.1, 252.3, 252.34; 935/22, 59, 64, 66, 72

[56] References Cited

U.S. PATENT DOCUMENTS

| | | | |
|---|---|---|---|
| 4,483,923 | 11/1984 | Blair | 435/253.3 |
| 4,996,155 | 2/1991 | Sick et al. | 435/252.3 |

OTHER PUBLICATIONS

Drahos et al. "Tracking Recombinant Organisms in the Environment. β–Galactosidase as a Selectable Non–antibiotic Marker for fluorescent *Pseudomonads*, " 4:439–444. (May/1986) Bio/Technology.

Webster's Dictionary, ninth edition, p. 626. Mish, F.C,ed Merriam–Webster, Inc. Springfield, Mass. (1990).

Watrud et al., Cloning of the *Bacillus thuringiensis* subsp. *Kurstaki* Delta–Endotoxin Gene Into *Pseudomonas Fluorescens*: Molecular Biology and Ecology of an Engineered Microbial Pesticide, Engineered Organisms in the Environment: Scientific Issues, American Society for Microbiology, Washington, D.C., 1985, pp. 40–46.

Kellogg et al., Plasmid Assisted Molecular Breeding: New Technique for Enhanced Biodegradation of Persistent Toxic Chemicals, Science, 214, 1981, pp. 1133–1135.

Mondello, F.J., Cloning and Expression in *Escherichia coli* of *Pseudomonas* Strain LB400 Genes Encoding Polychlorinated Biphenyl Degradation, J. Bacteriol., 171, 1989, pp. 1725–1732.

Bedard, et al., Rapid Assay for Screening and Characterizing Micro–organisms for the Ability to Degrade Polychlorinated Biphenyls, Appl. Environ. Microbiol., 51, 1986, pp.761–768.

Furukawa et al., cloning of a Gene Cluster Encoding Biphenyl and Chlorobiphenyl Degradation in *Pseudomonas pseudoalcaligenes*, J. Bacteriol., 166, 1986, pp. 392–398.

Winter et al., Efficient Degradation of Trichloroethylene by a Recombinant *Eschericchia coli*, Bio/Technology, 7, 1989, pp. 282–285.

Giger et al., 4–Nonylphenol in Sewage Sludge: Accumulation of Toxic Metabolites form Nonionic Surfactants, Science, 225, 1984, pp. 623–625.

Kohler et al., Cometabolism of Polychlorinated Biphenyls: Enhanced Transformation of Aroclor 1254 by Growing Bacterial Cells, Appl. Environ. Microbiol., 54–8, 1988, pp. 1940–1945.

Walter et al., A Method to Evaluate Survival of Genetically Engineered Bacteria in Soil Extracts, Current Microbiology, 15, 1987, pp. 193–197.

Bopp, L. H., Degradation of Highly Chlorinated PCBs by *Pseudomonas* Strain, J. Indus. Microbiol., 1, 1986, pp. 23–29.

Rattray et al., Luminescence–Based Nonextractive Technique for In Situ Detection of *Escherichia coli* in Soil, App. Environ. Micro–biol., 56–11, 1990, pp. 3368–3374.

Salonius et al., The Mutual Growth of *Arthrobacter Globiformis* and *Pseudomonas Fluorescens* in Gamma–Sterilized Soil, J. of Plant and Soil, , J. of Plant and Soil, 32, 1970, pp. 316–326.

Brunner et al., Enhanced Biodegradation of Polychlorinated Biphenyls in Soil by Analog Enrichment and Bacterial Inoculation, J. Environ. Qual. 14–3, 1985, pp. 324–328.

Ditta et al., Plasmids Related to the Broad Host Range Vector, pRK290, Useful for Gene Cloning and for Monitoring Gene Expression, 13, 1985, pp. 149–153.

Sanglard et al., Role of Extracellular Ligninases in Biodegradation of Benzo (a) pyrene by *Phanerochaete Chrysosporium*, Enzyme Microb. Technol., 8, 1986, pp. 209–212.

Keen et al., Improved Broad–host–range Plasmids for DNA Cloning in Gram–negative Bacteria, Gene, 70, 1988, pp. 1911–197.

Atlas and Bartha, Microbial Ecology: Fundamentals and Applications, Second Edition, Benjamin/Cummings Pub. Co., Inc., pp. 426–428.

Alexander, M., Introduction to Soil Microbiology, Second Edition, John Wiley and Sons Publishing, pp. 405–422.

*Primary Examiner*—Nancy Degen
*Attorney, Agent, or Firm*—Mathews, Collins, Shepherd & Gould, P.A.

[57] ABSTRACT

Recombinant microorganisms which produce non-adaptive proteins in a mixed, microbiologically competitive environment and which utilize a selective substrate are disclosed as field application vectors.

3 Claims, No Drawings

FIELD APPLICATION VECTORS

The present invention pertains to methods of producing proteins in a mixed, microbiologically competitive environment, for which environment the proteins are non-adaptive. In addition, the present invention relates to recombinant microorganisms which produce the proteins, and to methods of producing the microorganisms.

A major goal of environmental biotechnology is to produce highly competent strains of microorganisms which express particular gene products in mixed, competitive environments. The use of recombinant DNA techniques has facilitated the study of various pathways, but serious obstacles remain for the effective application of genetically engineered microorganisms in the field.

It is desirable to introduce recombinant microorganisms into particular environments so the proteins synthesized by the microorganisms can affect their intended targets. The ability to manipulate microorganisms so they are capable of proliferating in a mixed, microbiologically competitive environment has thus far produced disappointing results. A deliberately introduced recombinant microorganism must compete with the myriad other microorganisms indigenous to that environment for the limited supply of available energy sources. As a result, the supply of available carbon and energy becomes depleted to levels insufficient to sustain the recombinant microorganism. The recombinant microorganism fails to proliferate, thereby reducing its effective activity and preventing the expression of the protein at levels sufficient to substantially affect the intended targets.

One mode of increasing the amount of protein expressed in a particular environment is to repeatedly supplement the environment with additional recombinant microorganisms which express the desired protein. This tactic is somewhat self-defeating since the additional recombinant microorganisms will compete with the originally deployed recombinant microorganisms for the limited available substrates, thereby reducing the proliferation of the originally deployed microorganisms. Further, the added organisms and their pre-formed enzymes tend to become a ready food supply for the indigenous biota.

An alternative method is to supplement the environment with non-specific energy sources such as glucose. This is similarly undesirable since such non-specific substrates enhance the proliferation of competing indigenous microorganisms as well as and in preference to the recombinant microorganisms.

The present invention overcomes the problems encountered heretofore and provides methods for efficiently producing non-adaptive proteins in mixed, microbiologically competitive environments. A microorganism which is capable of utilizing a selective substrate in a mixed, microbiologically competitive environment possesses a distinct competitive advantage over the indigenous microorganisms in that it does not have to compete for the available carbon and energy sources. The present invention takes advantage of the existence of a finite lag time during which Darwinian selection forces operate in the environment. This lag time creates a temporary niche for the transformed microorganism thereby permitting adequate expression of the desired protein to affect the desired change in the environment.

The present invention also relates to recombinant microorganisms which express non-adaptive proteins in mixed, microbiologically competitive environments, and relates further to methods of producing the recombinant microorganisms.

Recombinant bacteria which express enzymes degradative of toxic waste chemicals (such as PCBs, 2,4,5-T, trichloroethylene, etc.) have been studied and characterized.

Kellogg et al., Science 214:1133–1135 (1981), reported the development of recombinant bacterial strains capable of totally degrading 2,4,5-trichlorophenoxyacetic acid by using the compound as their sole source of carbon at high concentrations.

Brunner et al., J. Environ. Qual. 14:324–328 (1985), reported that when cultures of Acinetobacter P6 were enriched with biphenyl analogs of the target PCBs, the adaptive enzymes produced by the microorganism were able to oxidize the aromatic ring but unable to completely degrade PCBs.

Furukawa et al., J. Bacteriol. 166, 392–398 (1986), reported the cloning of biphenyl and PCB catabolism genes into Pseudomonas pseudoalcaligenes.

Kohler et al., Appl. Environ. Microbiol. 54, 1940–1945 (1988), reported enhanced degradation of Aroclor 1254 by bacteria which cometabolized biphenyl compounds.

Mondello, J. Bacteriol. 171, 1725–1732 (1989), cloned and expressed genes from Pseudomonads encoding PCB degradative enzymes into E. coli.

However, when these bacteria are introduced into the hazardous waste field, they show limited or no growth, resulting in the insufficient production and application of the degradative enzymes. The addition of a growth substrate such as biphenyl is environmentally detrimental since biphenyls, themselves, are toxic to humans.

The growth and lifespan of a microorganism can be significantly reduced if it expresses proteins which are not beneficial to sustain the microorganism's life in the environment. That is, the expression of a non-adaptive protein depletes the microorganism of energy necessary to sustain life. If the desired protein does not participate in catabolizing the available carbon and energy sources, or in some other way protect or enhance the growth of the microorganism, then the microorganism receives no benefit of having expressed the protein and succumbs to a depletion of available energy sources.

In order to ensure a clear and uniform understanding of the description of the present invention and the appended claims, and also of the scope to be accorded to therein, the following definitions are set forth.

"Recombinant microorganism" means any heterotrophic bacterial, mammalian, insect, yeast, fungal, or other cell that has been transformed with DNA from a foreign source using recombinant technology.

"Non-adaptive protein" means a protein that does not contribute to the survival of the host microorganism in the particular environment in which the microorganism is placed. Conversely, an "adaptive protein" is a protein expressed by a microorganism which facilitates survival of the microorganism in the particular environment.

"Mixed, microbiologically competitive environment" means an environment that (i) is either native or foreign to the recombinant microorganism, (ii) is either natural or synthetic, and (iii) is populated by other microorganisms which compete for the available carbon and energy sources.

"Pseudomonas paucimobilis" means a bacterial strain isolated and identified as such using the API Rapid NFT Test (Analytab Products, Plainview, N.Y.).

"Selective substrate" means a substance that either is not normally utilized or is poorly utilized by microorganisms indigenous to the environment but is utilizable by the recombinant microorganism as a carbon and energy source. In other words, a selective substrate is a substance which by design is (i) utilized by the microorganism as a growth substrate but (ii) is not normally or is poorly utilized as a growth substrate by microorganisms indigenous to the environment.

"Field application vector" means the combination of a recombinant microorganism and selective substrate wherein the recombinant microorganism utilizes the selective substrate and expresses a non-adaptive protein in a mixed, microbiologically competitive environment.

The present invention pertains to a method of producing a non-adaptive protein in a mixed, microbiologically competitive environment. According to the invention, a recombinant microorganism is introduced into the environment in the presence of a selective substrate. The recombinant microorganism (i) utilizes the selective substrate and (ii) expresses a protein which is non-adaptive for the organism in that environment. In the present invention, either or both of (i) and (ii) are properties conferred by exogenous DNA transformed into the microorganism using recombinant technology.

The present invention also pertains to recombinant microorganisms which (i) express a non-adaptive protein in the particular mixed, microbiologically competitive environment in which it is placed, and (ii) is capable of utilizing a selective substrate.

The recombinant microorganisms according to the present invention can be produced by first identifying a microorganism which can utilize a selective substrate. A second microorganism which expresses the desired protein then is identified. While the expressed protein can be and probably is adaptive with respect to the second microorganism, it is non-adaptive for the recombinant microorganism in the mixed, microbiologically competitive environment in which the host microorganism will be placed. Either of the two microorganisms is then transformed with a gene or genes that confer the relevant capability of the other microorganism. Alternatively, a third microorganism can be transformed with the genes that confer the relevant capabilities of the first and second microorganisms.

Any microorganism which can utilize a selective substrate and stably take up and maintain exogenous plasmid DNA is suitable for use in the present invention. In addition, any microorganism which is capable of expressing useful non-adaptive proteins into the environment into which the microorganism is introduced can be used. It is a matter of design which phenotype is chosen. Indeed, it is within the scope of the present invention to transform one of the microorganisms with the relevant genetic capability of the other, thereby arriving at a single microorganism that possesses the phenotypical characteristics of both.

The DNA of the recombinant microorganisms of the present invention can include a promoter sequence regulated by the substrate. The promoter sequence is located upstream of the gene encoding the protein so as to cause the expression of the protein in the presence of the substrate.

The selective substrates suitable for use in the present invention typically are those not commonly found in the particular environment in which the recombinant microorganism is to be placed. Such substrates include both synthetically produced organic compounds and naturally occurring organic compounds that have been synthetically modified.

Considerable information is available relating to the biodegradation of synthetic compounds and this can be used to select appropriate substrates. This information has been accumulated based on studies of accidental release of synthetic compounds into the terrestrial environment, biodegradability of consumer products intentionally released through sewage treatment plants, and biodeterioration of materials stored or used in the environment.

Compounds suitable for use as selective substrates include, for example, surfactants; organic colorants; polymers such as polyethylene, propylene, polystyrene, polyamides, polyesters, and polyurethanes; plasticizers; rubbers; regenerated proteins; regenerated and modified celluloses; bitumen; adhesives; sealants; fuels; lubricants; and paints; or individual components of these. Preferably, the selective substrate compounds are non-toxic.

The type of environment in which the microorganism is to be introduced should be considered in the selection of the microorganism. It should be readily apparent that some microorganisms are better suited for certain environmental conditions than others. However, this should not totally preclude the use of some microorganisms in certain environments since intentional genetic alterations in the microorganism can be made to confer the desired growth characteristics.

According to the present invention, a non-adaptive protein is produced by a recombinant microorganism in a mixed, microbiologically competitive environment. Whether a protein is adaptive or non-adaptive according to the present invention depends upon the phenotypical characteristics of the host microorganism and the nature of the particular environment. For example, a protein conferring resistance to a specific antibiotic is non-adaptive for environments where the specific antibiotic does not threaten the host microorganism. In addition, 2,3-dioxygenase; dihydrodioldehydrogenase; 2,3-dihydroxybiphenyl dioxygenase; and 2-hydroxy-6-oxo-6-phenylhexa-2,4-dienoic acid hydrase are non-adaptive enzymes for PCB contaminated environments in the absence of sufficient concentrations of biphenyl, since the host microorganism does not utilize the degraded PCB products as carbon and energy sources. Other non-adaptive gene products for the host can include for example, delta-endotoxins such as those of *Bacillus thuringiensis,* chitinase, laminarinase, pyrethrins, rotenone, baculovirus, various hormones, and pheromones. These compounds are useful as biopesticides in protecting crop environments.

In the method of the present invention, the recombinant microorganism is introduced, in the presence of the selective substrate, into a microbiologically competitive environment. Various means for deliberately introducing microorganisms into certain environments are known per se. For example, terrestrial environments can be sprayed or flooded with liquid media containing the recombinant microorganisms. The method chosen for introducing the microorganisms into an environment should be such that the microorganisms are not disrupted or injured during the process.

As noted above, the recombinant microorganisms are introduced into an environment in the presence of a selective substrate. The selective substrate can be introduced either simultaneously with the recombinant microorganisms, or in sufficiently close temporal proximity thereto, before or after, to be available as an energy source for the recombinant microorganism. Any known method for introducing a compound into an environment can be used. It is possible that the selective substrate may be independently introduced into the particular environment, in which case, the microorganisms are introduced shortly thereafter so as to minimize the competition from any indigenous microorganisms which may adapt to the substrate.

Once the recombinant microorganisms and the selective substrate are present in the particular environment, the recombinant microorganisms utilize the selective substrate as a carbon and energy source and thus are able to proliferate with little competition from indigenous microorganisms, which cannot utilize the selective substrate. The growth without substantial competition of the recombinant microorganisms results in an efficient expression of the non-adaptive proteins into the environment, where the proteins can affect their intended targets.

The present invention is suitable, for example, in the degradation of xenobiotics using cometabolic pathways. Typical xenobiotics include, for example, polychlorinated biphenyl compounds (PCBs); trichloroethylene (TCE); parathion; N-methylcarbamate insecticides; benzopyrene; 1,1'-(2,2,2-trichloroethylidene)bis[4-chlorobenzene] (DDT); 2,3,-7,8-tetrachlorodibenzo-p-dioxin; 1,2,3,4,5,6-hexachlorocyclohexane (Lindane); 1,4,5,6,7,8,8-heptachlor-3a-4,7,7a-tetrahydro-4,7-methanoindene (Heptachlor); and 1,2,3,4,10,10-hexachloro-1,4,4a,5,8,8a-hexahydro-1,4:5,8-dimethanonaphthalene (Aldrin).

Genes encoding enzymes operable to degrade PCBs, TCE, parathion and N-methylcarbamate insecticides are known. By way of example, Mondello, supra., which is incorporated herein by reference, describes the plasmid pGEM410 which encodes all of the genes required to convert PCBs to chlorobenzoic acids. The gene bphA encodes biphenyl 2,3-dioxygenase, the bphB gene encodes dihydrodioldehydrogenase, the bphC gene encodes 2,3-dihydroxybiphenyl dioxygenase, and the bphD gene encodes 2-hydroxy-6-oxo-6-phenylhexa-2,4-dienoic acid hydrase. Genes for biphenyl and PCB degradation have also been described by Ahmad et al. (1990) *Gene* 86, 53–61; Furukawa et al. (1986) *J. Bacteriol.* 166, 392–398; Hayase et al. (1990) *J. Bacteriol.* 172, 1160–1164; Khan et al. (1988) *Appl. Environ. Microbiol.* 54, 2664–2671; Khan et al. (1990) *Appl. Environ. Microbiol.* 56, 956–962; Kimbara et al. (1989) *J. Bacteriol.* 171, 2740–2747; and Mondello (1989) *J. Bacteriol.* 171, 1725–1732, all of which are incorporated herein by reference.

In addition, the following references describe various mechanisms which utilize aromatic hydrocarbons as carbon and energy sources: Burlage et al. (1989) *Appl. Environ. Microbiol.* 55, 1323–1328; Cerniglia et al. (1990) *Metabolism of Polyacrylic Aromatic Hydrocarbons in the Aquatic Environment*, ed. Varanasi, U. (CRC Press, Boca Raton, Fla.), pp. 41–68; Dagley (1986) *The Bacteria*, v. 10, ed. Gunsalus et al. (Academic Press, New York), pp. 527–556; Ghosal et al. (1985) *Science* 228, 135–142; Gibson et al. (1984) *Microbial Degradation of Organic Compounds*, ed. Gibson (Marcel Dekker, New York ), pp. 181–251; Guengerich (1990) *CRC Crit. Rev. Biochem. Molec. Biol.* 25, 97–153; and Sariaslani (1989) *CRC Crit. Rev. Biotech.* 9, 171–257 which are incorporated herein by reference. Kurkela et al. (1988) *Gene* 73, 355–362 and Serdar et al. (1989) *Biochem. Biophys. Res. Commun.* 164, 772–779 describe naphthalene degradation which are incorporated herein by reference. Bartilson et al. (1990) *Mol. Gen. Genet.* 220, 294–300 and Kukor et al. (1990) *J. Bacteriol.* 172, 4624–4630 describe phenol degradation which are incorporated herein by reference. Irie et al. (1987) *Agric. Biol. Chem.* 51, 1489–1493 describe benzene degradation which is incorporated herein by reference. Franklin et al. (1981) *Proc. Natl. Acad. Sci. USA* 78, 7458–7462; McCombie (1984) *Abstr. Annu. Meet. Am. Soc. Microbiol.*, p. 155; Stephens et al. (1989) *FEMS Microbiol. Lett.* 57, 295–300; Winter et al. (1989) *Bio/Technology* 7, 282–285; and Zylstra et al. (1988) *Appl. Environ. Microbiol.* 54, 1498–1503 describe toluene degradation which are incorporated herein by reference. Jeenes et al. (1982) *J. Bacteriol.* 150, 180–187; Ramos et al. (1986) *Proc. Natl. Acad. Sci. USA* 83, 8467–8471; Ramos et al. (1987) *Science* 235, 593–596; Reineke et al. (1982) *J. Bacteriol.* 150, 195–201; and Rojo et al. (1987) *Science* 238, 1395–1398 describe hybrid pathways for routes of degradation using cloned genes which are incorporated herein by reference. Williams et al. (1974) *J. Bacteriol.* 120, 416–423 and Worsey et al. (1975) *J. Bacteriol.* 124, 7–13 describe the TOL plasmid which are incorporated herein by reference. *Pseudomonas mendocina* KR is described in Whited (1986) *Ph.D. Thesis*. University of Texas at Austin, 1986 which is incorporated herein by reference. *Pseudomonas cepacia* G4 is described in Shields et al. (1989) *Appl. Environ. Microbiol.* 55, 1624–1629 which is incorporated herein by reference. *Pseudomonas putida* F1 is described in Gibson et al. (1968) *Biochemistry* 7, 2653–2662 and Gibson et al. (1970) *Biochemistry* 9, 1626–1630 which are incorporated herein by reference. The above genes are especially suitable for transformation into microorganisms which utilize a selective substrate according to the present invention. Likewise, additional genes which encode degradative enzymes that are yet to be discovered are suitable for the present invention once the genes are properly characterized.

By combining in a microorganism the ability to express the degradative enzymes with the capability of utilizing a selective substrate, a microorganism can be obtained which can be efficiently used for the bioremediation of hazardous waste sites. Introducing the recombinant microorganisms in the presence of a selective substrate into the application field enhances the proliferation of the recombinant microorganisms causing the efficient production of the useful enzymes. Indeed, it is not necessary, when using the present invention for hazardous waste bioremediation, to utilize an analog of the target xenobiotic as a substrate.

The present invention also is suitable for degrading xenobiotics which typically are found in the environment at concentrations below that which will support microbial growth. Such low concentration xenobiotics include 2,4,5-trichlorophenoxyacetic acid, naphthalene, toluene, aliphatic hydrocarbons, halogenated aliphatic hydrocarbons, polycyclic aromatic hydrocarbons, chloroaromatics, organochlorine pesticides, and organophosphorus pesticides. Genes encoding the enzymes operable to degrade, for example, 2,4,5-trichlorophenoxyacetic acid, naphthalene, toluene, and aliphatic hydrocarbons are known as stated above and are suitable for transformation into microorganisms which utilize selective substrates according to the present invention.

When using the present invention for the production of enzymes for the degradation of xenobiotics, preferred selective substrates are surfactants. Also preferred are detergents, which are not readily utilized by most indigenous soil microorganisms, and which offer an additional capability of assisting in the solubilization of the contaminating chemicals. In addition, the host microorganisms preferably are Pseudomonads. Also preferred is *Pseudomonas paucimobilis*.

In addition to the above, the present invention is particularly applicable for the field production of biological pesticides. Typical biological pesticides include, for example, the delta-endotoxins, such as *Bacillus thuringiensis;* and other toxins such as chitinase, laminarinase, pyrethrins, rotenone, baculovirus, and various hormones and pheromones. The gene encoding *Bacillus thuringiensis* delta-endotoxin is known and reported by Watrud et al., Engineered Organisms in the Environment: Scientific Issues, American Society for Microbiology, Washington, D.C., 1985, pp. 40–46, which is incorporated herein by reference. It is readily apparent that other genes encoding toxins yet to be discovered also can be used in the present invention once the genes are properly characterized.

Combining the capability to utilize a selective substrate with the ability to express compounds having the appropriate pesticidal properties produces a microorganism which can be applied with the selective substrate to a crop field in order to selectively control pests.

The recombinant microorganisms according to the present invention which are capable of utilizing a particular selective substrate can be prepared by developing cultures using an enrichment method similar to the plasmid assisted molecular breeding technique of Kellogg et al., *Science* 214, 1133–1135, (1981) which is incorporated herein by reference. In general, non-sterile, mixed culture samples of the application or similar environment are inoculated with a variety of the other non-sterile materials potentially containing desirable microorganisms. Different substrates then are added to the cultures and the microbial populations are allowed to develop for several weeks. After several transfers in fresh medium, strains capable of using the substrate as a sole source of carbon and energy are isolated, identified and grown in pure culture. Those substrates which are utilized by the microorganisms and which are not normally or are poorly utilized by the indigenous microbial community are considered as potential selective substrates.

Once a series of cultures is identified with the desired characteristics, they are evaluated for their ability to take up and stably maintain plasmid DNA. Broad-host range plasmids containing antibiotic resistance markers are introduced into the cells by transformation or conjugation using methods known per se. Such broad-host range plasmids suitable for use in the present invention are the type known per se, and taught, for example, by Mondello, F. J., *J. Bacteriol.* 171, 1725–1732 (1989); and by Furukawa et al., *J. Bacteriol.* 166, 392–398, (1986), which are incorporated herein by reference. The efficiency of the uptake of the plasmids then is determined by culturing the transformed microorganisms in the presence of the antibiotic. Cultures showing the most favorable characteristics of stable DNA maintenance are transformed with plasmids containing the desired gene and grown in culture. Improvements in the strain can include integration of the desired genes into the host chromosome, and replacement of the normal promoter with a regulated promoter, such as one regulated by the selective substrate. The methods used to clone the genes, and select, transform, and culture the cells are known per se and are not considered part of this invention.

The particular environment then is inoculated, using known procedures, with the transformed host strain and the selective substrate. The inoculation rate of the microorganisms will, of course, depend upon the particular environment, the desired effective concentration of non-adaptive proteins, and the concentration of the target material in the environment. The inoculation rate of the selective substrate will depend upon what is necessary to sustain the growth of inoculated microorganisms in the environment. Since the host microorganisms have finite lifespans and a finite supply of substrate, subsequent supplementation of the environment with additional transformed hosts and/or selective substrate also can be made.

The following examples are provided to illustrate the nature of the present invention and are not to be construed as limiting the scope thereof, which scope is specifically defined in the appended claims.

EXAMPLE 1

Selective Substrate Determination

Several detergents representing a spectrum of biodegradation resistance were chosen as potential selective substrates. Six nonionic and seven anionic detergents were obtained which varied in structural complexity, number of repeating units, and compositional homogeneity. The sources and chemical formulae of the detergents, and their corresponding abbreviations are indicated in Table I. The majority of the nonionic detergents are variations of the alkylphenoxypoly(ethyleneoxy)ethanol type, whereas most of the anionic detergents are sulfates or sulfonates. Micro-Step H-301 (sulfonate) is listed in Table I as an anionic detergent due to its structural similarity to members of the anionic group, even though the mixture is described by the manufacturer as a nonionic blend.

TABLE I

| Detergent Abbreviations, Trade Names, Manufacturers and Structural Information | |
|---|---|
| | NONIONIC DETERGENTS |
| TWN | Tween 80 (Aldrich)<br>Polyoxyethylene (20) sorbitan monooleate |
| IPL | Igepal CO-520 (Aldrich)<br>$4\text{-}(C_9H_{19})C_6H_4O(CH_2CH_2O)_4CH_2CH_2OH$ |
| TNX | Triton-X-100 (Fisher)<br>$C_8H_{17}(C_6H_4)OCH_2CH_2)_xOH$ (X = 10 average) |
| IGP | Igepal CO-720 (Aldrich)<br>$4\text{-}(C_9H_{19})C_6H_4O(CH_2CH_2O)_{11}CH_2CH_2OH$ |
| ICO | Igepal CO-890 (Aldrich)<br>$4\text{-}(C_9H_{19})C_6H_4O(CH_2CH_2O)_{39}CH_2CH_2OH$ |
| IDM | Igepal DM-97O (Aldrich)<br>Dialkylphenoxypoly(ethyleneoxy)ethanol |
| | ANIONIC DETERGENTS |
| MSH | Micro-Step H-301 (Stepan)<br>Sulfonate, non-ionic blend |
| DS | Dodecyl sulfate, sodium salt (Aldrich)<br>$CH_3(CH_2)_{11}OSO_3Na$ |
| LAS | N-Lauroylsarcosine, sodium salt (Sigma)<br>N-Dodecanoyl-N-Methylglycine |
| PS11 | Polystep A-11 (Stepan)<br>Isopropyl amine branched dodecylbenzene sulfonate |
| DOS | Dioctyl sulfosuccinate, sodium salt (Sigma)<br>Sulfosuccinic acid bis[2-ethyl-hexyl] ester |
| PS | Polystep A-16 (Stepan)<br>Branched sodium dodecylbenzene sulfonate |
| TDS | Stepantan DT-60 (Stepan)<br>Triethanolamine dodecylbenzene sulfonate |

Soil collected from sites previously exposed to aliphatic and aromatic hydrocarbons and detergents were used to inoculate 4-liter batches of PAS media (Bopp, L. H., *J. Indust. Microbiol.* 1, 23–29, 1986) amended with common household detergents, fuel oil, creosote, ethyl glycol, and Tween 80. Batch cultures were established by back-mixing individual enrichment cultures for the detergents listed in Table I and various other detergents. The detergents included dodecylamine hydrochloride, dodecyltrimethylammonium bromide, benzalkonium chloride, 1-dodecylpyridinium chloride monohydrate, cetylpyridinium bromide monohydrate, hexadecyltrimethylammonium bromide, didecyldimethylammonium bromide, and benzethonium chloride. Other included compounds were the sodium salts of caprylic acid, dodecylbenzenesulfonic acid, and cholic acid, Ninate 401, 2-benzylcarboxylic acid, 2,5-hexanediol, poly(ethylene glycol), poly(vinyl alcohol), nonyl phenol, glycerine liquid soap, and Dawn® dishwashing liquid. In total, five of these batch cultures were established containing mixtures of varying amounts of thirty detergents and related compounds.

Inocula from the five batch cultures were mixed with 50 ml of PAS media amended with individual detergents (0.2 or 1.0%) as the sole source of carbon and energy. The mixtures were incubated at room temperature. Distilled water was added as needed to replace any evaporative losses. Upon the development of turbidity, 0.2 ml of the culture was transferred to fresh media, and incubated as before. This process was repeated a total of three times to select for the most rapidly growing strains.

Upon an increase in turbidity, serial dilutions of 1 ml of culture in dilution water (Standard Methods for the Examination of Water and Wastewater, 16th ed., 1985, American Public Health Association, Washington, D.C.) were prepared, and plated on noble agar containing PAS medium and filter-sterilized detergent. Following incubation at 25° C., five individual colonies for each detergent were restreaked onto R2A agar (Difco). One colony from each of these five plates was again streaked onto detergent containing agar. One colony from each of these detergent plates then was transferred to a R2A agar slant and a detergent-agar slant for storage at 4° C. Five isolates then were obtained for each detergent.

The five isolates for each detergent were screened for growth rates, morphology, motility, and gram stain. Growth rate was determined in PAS medium with filter-sterilized detergent as the sole source of carbon and energy. Each isolate was mixed from the detergent slant into 4 ml of media. The mixtures were incubated at room temperature. The culture was suspended and absorbance was measured at 660 nm using a spectrophotometer (Bausch and Lomb, Spectronic 20). When the absorbance reached 0.5, 0.1 ml of the culture was incubated, as above, and the growth rate measured as the rate of increase in absorbance at 660 nm.

For those isolates which grew to an absorbance of 0.5, gram stain, morphology, and motility were determined. Gram staining was performed using a Fisherbrand gram stain kit (Fisher Scientific, Pittsburgh, Pa.) with positive and negative controls. Morphology and motility were determined.

One isolate for each detergent was selected for further experimentation. The criteria for selection were a high growth rate to a high absorbance level. For ease in genetic transformation, the organism selected was gram negative. Members of the genus Pseudomonas were isolated.

The competitive potential of each detergent degrading organism was assessed indirectly using Warburg respirometry. The rate of oxygen consumption in the detergent amended soil inoculated with the respective detergent degrading isolate was compared to the rate of oxygen consumption in a control sample containing the same detergent amended soil to which an autoclaved inoculum was added. This control sample was used to determine the detergent degradation rate by the indigenous soil microbial population.

Soil characteristics are listed in Table II. Fresh soil was collected and passed through a 4.75 mm sieve. Soil pH was determined using the 0.01M $CaCl_2$ method (Peech, 1965), and adjusted to pH 7 with calcium hydroxide, if necessary. The soil was dried to a moisture content of 40% of field capacity.

TABLE II

Characterization of Soil
Used in Warburg Respirometry Experiments

| | |
|---|---|
| Organic Matter (%) | 4.0 |
| Carbon (%) | 2.3 |
| Sand (%) | 34.0 |
| Silt (%) | 40.0 |
| Cation Exchange Capacity (meq/100 g) | 10.5 |
| Exchange Cations (meq/100 g) | |
| Mg | 3.9 |
| K | 1.0 |
| Ca | 9.2 |
| pH | 6.5–7.0 |
| TKN (%) | 0.2 |
| N (% as organic matter) | 4.8 |
| Mg (mg/kg) | 500.0 |
| P (mg/kg) | 82.0 |
| K (mg/kg) | 242.0 |
| Ca (mg/kg) | 2,075.0 |
| Field Capacity (% moisture) | 23.0 |

For each detergent/organism combination, 50 g of soil was prepared by adding fertilizer ($NH_4Cl$, 169 ppm; $K_2HPO_4$, 42 ppm), detergent (0.2 or 1.0%, wet weight detergent/wet weight soil) and sufficient distilled water to achieve a final moisture content of 65% of field capacity. The soil was mixed, and 20 g subsamples were inoculated with live or autoclaved detergent degrading organisms. Soil samples were also prepared without detergent amendment for the determination of background $O_2$ consumption, and enumeration of the natural soil microbial populations by heterotrophic plate count (R2A agar).

The inoculum was cultured in 4 ml of detergent/PAS medium and mixed. The detergent concentration in this medium was the same as that applied to the soil. When an absorbance of 0.5 was achieved, 2 ml was transferred to another tube and autoclaved. For the detergent PS11, the inoculum was grown on HPC medium (0.5% tryptone, 0.25% yeast extract, 0.1% glucose), centrifuged, and resuspended in dilution water. To each 20 g subsample of detergent amended soil, 0.2 ml of the appropriate culture (live or autoclaved) was added. The concentration of cells in the inoculum was determined by plate counting on R2A agar.

The 20 g subsamples were incubated at 25° C. Oxygen consumption was monitored over 2 to 8 hour periods, 1 to 4 times per day, depending on the rate of activity.

For the first two weeks of each experiment, the subsamples were recharged with oxygen every other day and the soil mixed. The potassium hydroxide solution (10% w/v) also was replaced. For the third and fourth week of incubation, the samples were recharged every 3 days.

All the detergent degrading organisms tested for competitive potential were identified using the Rapid NFT Test (api Analytab Products, Plainview, N.Y.) in accordance with the manufacturer's instructions.

The results of the Rapid NFT Tests and the growth curves for the fastest growing isolates on 1.0% TWN and 1.0% IGP are presented in FIG. 1. Analogous curves for organisms cultured on nonionic or anionic detergents at a concentration of 0.2% are presented in FIGS. 2 and 3, respectively.

The choice of which isolate to use for each detergent was based entirely on growth rate, since for each detergent, morphology, motility, and gram stain of the fastest growing isolates were the same. Seven of the ten species tested for competitive ability using Warburg respirometry were identified as members of the genus Pseudomonas.

The indigenous microbial population, as determined by heterotrophic plate count (R2A agar—9 day incubation), ranged from approximately $8.5 \times 10^7$ to approximately $2.2 \times 10^8$ cells/gram of soil at the start of the Warburg respirometry experiments. The applied inoculum concentration, calculated from heterotrophic plate count (R2A agar) determinations on inoculum cultures (absorbance—0.5), ranged from approximately $4.6 \times 10^5$ to approximately $3.1 \times 10^7$ cells/gram of soil.

The Warburg respirometry results of the competition experiments for the nonionic detergents are presented in FIGS. 4 and 5. The rate of detergent consumption in soil amended with 0.2% or 1.0% TWN, and inoculated with the respective TWN degrading isolates, was essentially the same as that of the uninoculated soil containing only the indigenous population. For the soils amended with 0.2% IPL, 0.2% TNX, 0.2% IGP, or 1.0% IGP, detergent consumption was faster and more extensive in the inoculated soil. A period of exponential growth was evident in the inoculated soil, followed by a decreasing rate of activity after approximately 200 hours. A similar period of exponential growth was not evident in the uninoculated soil. A background control was established which included soil that was neither amended with detergent nor inoculated with a detergent consuming culture (FIG. 4C). Oxygen consumption for this control is expressed as percent of 1.0% IGP consumed. Comparison of the consumption curves for the soil amended with 1.0% IGP and inoculated with autoclaved organisms (FIG. 4B—autoclaved inoculum) and the soil that was neither amended with detergent nor inoculated (FIG. 4C—no inoculum), indicates that the rate and extent of IGP consumption by the indigenous population was very low.

The Warburg respirometry results of the competition experiments for the anionic detergents are presented in FIG. 6. For soils amended with 0.2% MSH, the rate of consumption was initially the same in the inoculated and uninoculated soil. After 100 hours the extent of consumption was slightly higher in the inoculated soil. For 0.2% DS, the initial rate of consumption was higher in the inoculated soil, but the comparative lag in activity by the indigenous population was very short, and by 100 hours, more detergent had been consumed in the uninoculated soil. The pattern of oxygen consumption in the soils amended with 0.2% LAS was similar to that observed for 0.2% DS, except that the initial difference in consumption rate between the inoculated and uninoculated soils was greater. For 0.2% PS11, the initial rate of consumption was higher in the inoculated soil, but decreased rapidly after consumption of only 15% of the applied detergent. By the conclusion, only 20% of the detergent had been consumed (uncorrected for background $O_2$ consumption).

EXAMPLE 2

Enrichment, Isolation, and Screening of TWN (0.2%)/Potential Host Combination

The enrichment, isolation and screening procedures of Example 1 for a TWN (0.2%)/potential host combination, yielded a combination which exhibited high relative growth as estimated by visual examination of turbidity in detergent amended PAS medium. The combination also exhibited high growth of individual colonies on detergent plates, high relative growth of individual isolates in detergent amended PAS medium on rotary mixer, no difference in growth rate of detergent degrading isolates compared to the natural population in detergent amended soil as suggested by $O_2$ consumption, and had acceptable identification characteristics, as an *Acinetobacter calcoaceticus* on the Rapid NFT Test Ranking System.

EXAMPLE 3

Enrichment, Isolation, and Screening of TWN (1.0%)/Potential Host Combination

The enrichment, isolation and screening procedures of Example 1 for a TWN (1.0%)/potential host combination, yielded a combination which exhibited high relative growth as estimated by visual examination of turbidity in detergent amended PAS medium. The combination also exhibited high growth of individual colonies on detergent plates, high relative growth of individual isolates in detergent amended PAS medium on rotary mixer, no difference in growth rate of detergent degrading isolates compared to the natural population in detergent amended soil as suggested by $O_2$ consumption, and had good identification characteristics, as a *Pseudomonas testosteroni* on the Rapid NFT Test Ranking System.

EXAMPLE 4

Enrichment, Isolation, and Screening of IPL (0.2%) /Potential Host Combination

An IPL (0.2%)/potential host combination produced using the enrichment, isolation and screening procedures of Example 1 exhibited moderate relative growth as estimated by visual examination of turbidity in detergent amended PAS medium. The combination also showed high growth of individual colonies on detergent plates, a moderate relative growth of individual isolates in detergent amended PAS medium on rotary mixer, a high growth rate of detergent degrading isolates compared to the natural population in detergent amended soil as suggested by $O_2$ consumption, and had good identification characteristics, as a *Pseudomonas putida* on the Rapid NFT Test Ranking System.

EXAMPLE 5

Enrichment, Isolation, and Screening of TNX (0.2%)/Potential Host Combination

The enrichment, isolation and screening procedures of Example 1 for a TNX (0.2%)/potential host combination, yielded a combination which exhibited moderate relative growth as estimated by visual examination of turbidity in detergent amended PAS medium. The combination also exhibited high growth of individual colonies on detergent plates, moderate relative growth of individual isolates in detergent amended PAS medium on rotary mixer, high growth rate of detergent degrading isolates compared to the natural population in detergent amended soil as suggested by $O_2$ consumption, and had good identification characteristics on the Rapid NFT Test Ranking System.

EXAMPLE 6

Enrichment, Isolation, and Screening of IGP (1.0%) /Potential Host Combination

The enrichment, isolation and screening procedures of Example 1 were used to produce a IGP (1.0%)/potential host combination which showed moderate relative growth as estimated by visual examination of turbidity in detergent amended PAS medium. The combination also produced high growth of individual colonies on detergent plates, a moderate relative growth of individual isolates in detergent amended PAS medium on rotary mixer, and a high growth rate of detergent degrading isolates compared to the natural population in detergent amended soil as suggested by $O_2$ consumption. The combination also had good identification characteristics, as a *Pseudomonas paucimobilis* on the Rapid NFT Test Ranking System. It was identified as a strain of *Pseudomonas paucimobilis*, and given the identity of strain 1IGP4.

EXAMPLE 7

Enrichment, Isolation, and Screening of IGP (0.2%) /Potential Host Combination

The enrichment, isolation and screening procedures of Example 1 for a IGP (0.2%)/potential host combination, yielded a combination which exhibited moderate relative growth as estimated by visual examination of turbidity in detergent amended PAS medium. The combination also exhibited high growth of individual colonies on detergent plates, moderate relative growth of individual isolates in detergent amended PAS medium on rotary mixer, high growth rate of detergent degrading isolates compared to the natural population in detergent amended soil as suggested by $O_2$ consumption, and had good identification characteristics, as a *Pseudomonas paucimobilis* on the Rapid NFT Test Ranking System.

EXAMPLE 8

Enrichment, Isolation, and Screening of ICO (0.2%)/Potential Host Combination

An ICO (0.2%)/potential host combination produced using the enrichment, isolation and screening procedures of Example 1 yielded no relative growth as estimated by visual examination of turbidity in detergent amended PAS medium.

EXAMPLE 9

Enrichment, Isolation, and Screening of IDM (0.2%)/Potential Host Combination

The enrichment, isolation and screening procedures of Example 1 for a IDM (0.2%)/potential host combination, produced a combination which showed no relative growth as estimated by visual examination of turbidity in detergent amended PAS medium. The combination also exhibited high growth of individual colonies on detergent plates, and had no relative growth of individual isolates in detergent amended PAS medium on rotary mixer.

EXAMPLE 10

Enrichment, Isolation, and Screening of MSH (0.2%)/Potential Host Combination

The enrichment, isolation and screening procedures of Example 1 for a MSH (0.2%)/potential host combination, yielded a combination which exhibited high relative growth as estimated by visual examination of turbidity in detergent amended PAS medium. The combination also exhibited high growth of individual colonies on detergent plates, high relative growth of individual isolates in detergent amended PAS medium on rotary mixer, and showed no difference in growth rate of detergent degrading isolates compared to the natural population in detergent amended soil as suggested by $O_2$ consumption. The combination displayed acceptable identification characteristics, as an *Acinetobacter calcoaceticus* on the Rapid NFT Test Ranking System.

EXAMPLE 11

Enrichment, Isolation, and Screening of DS (0.2%)/ Potential Host Combination

The enrichment, isolation and screening procedures of Example 1 for a DS (0.2%)/potential host combination, yielded a combination which exhibited high relative growth as estimated by visual examination of turbidity in detergent amended PAS medium. The combination also exhibited high growth of individual colonies on detergent plates, high relative growth of individual isolates in detergent amended PAS medium on rotary mixer, low growth rate of detergent degrading isolates compared to the natural population in detergent amended soil as suggested by $O_2$ consumption, and had good identification characteristics, as a *Pseudomonas fluorescens* on the Rapid NFT Test Ranking System.

EXAMPLE 12

Enrichment, Isolation, and Screening of LAS (0.2%)/Potential Host Combination

A LAS (0.2%)/potential host combination produced using the enrichment, isolation and screening procedures of Example 1, exhibited moderate relative growth as estimated by visual examination of turbidity in detergent amended PAS medium. The combination also exhibited high growth of individual colonies on detergent plates, a moderate relative growth of individual isolates in detergent amended PAS medium on rotary mixer, and moderate growth rate of detergent degrading isolates compared to the natural population in detergent amended soil as suggested by $O_2$ consumption. The combination displayed good identification characteristics, as a *Pseudomonas cepacia* on the Rapid NFT Test Ranking System.

EXAMPLE 13

Enrichment, Isolation, and Screening of PS11 (0.2%)/Potential Host Combination

The enrichment, isolation and screening procedures of Example 1 for a PS11 (0.2%)/potential host combination, yielded a combination which exhibited low relative growth as estimated by visual examination of turbidity in detergent amended PAS medium. The combination also exhibited high growth of individual colonies on detergent plates, low relative growth of individual isolates in detergent amended PAS medium on rotary mixer, high growth rate of detergent degrading isolates compared to the natural population in detergent amended soil as suggested by $O_2$ consumption, and had good identification characteristics, as an Achromobacter gr. VD. on the Rapid NFT Test Ranking System.

EXAMPLE 14

Enrichment, Isolation, and Screening of DOS (0.2%)/Potential Host Combination

The enrichment, isolation and screening procedures of Example 1 for a DOS (0.2%)/potential host combination, yielded a combination which exhibited no relative growth as estimated by visual examination of turbidity in detergent amended PAS medium.

EXAMPLE 15

Enrichment, Isolation, and Screening of PS16 (0.2%)/Potential Host Combination

A PS16 (0.2%)/potential host combination produced using the enrichment, isolation and screening procedures of Example 1 yielded a combination which exhibited no relative growth as estimated by visual examination of turbidity in detergent amended PAS medium. The combination also exhibited high growth of individual colonies on detergent plates, and no relative growth of individual isolates in detergent amended PAS medium on rotary mixer.

EXAMPLE 16

Enrichment, Isolation, and Screening of TDS (0.2%)/Potential Host Combination

The enrichment, isolation and screening procedures of Example 1 for a TDS (0.2%)/potential host combination, yielded a combination which exhibited no relative growth as estimated by visual examination of turbidity in detergent amended PAS medium. The combination also exhibited high growth of individual colonies on detergent plates, and no relative growth of individual isolates in detergent amended PAS medium on rotary mixer.

EXAMPLE 17

Growth of Pseudomonas paucimobilis Strains Having Antibiotic Resistance

The growth rate of Pseudomonas paucimobilis was determined in 4 ml of heterotrophic plate count medium (1.0% HPC medium; 0.5% tryptone, 0.25% yeast extract, 0.1% glucose in distilled water). Growth rate also was determined in PAS medium (Bopp, supra.) amended with 1.0% Igepal CO-720 (IGP; Aldrich Chemical Co., Milwaukee, Wis.), hereinafter referred to as "1.0% IGP medium." The inocula for growth rate determinations consisted of 0.1 ml of a culture of P. paucimobilis previously grown in 1.0% IGP medium to an absorbance of 0.5, as determined at 660 nm using a spectrophotometer (Bausch and Lomb, Spectronic 20). Growth rate was measured as the rate of increase in absorbance at 660 nm.

Warburg respirometry was used to indirectly compare the selectivity of 1.0% HPC and 1.0% IGP for P. paucimobilis in a competitive soil environment, and determine the extent of substrate consumption. Soil samples were amended with either 1.0% HPC or 1.0% IGP, and inoculated with either live or autoclaved P. paucimobilis. This inoculum was previously grown to an absorbance or 0.5 in 1.0% IGP medium. Control samples then were prepared containing soil with no substrate amendment, and inoculated with live or autoclaved P. paucimobilis. An additional control contained soil with neither substrate amendment nor an inoculum. The soil characteristics, method of soil preparation, and the Warburg apparatus operational methods have been previously described in Example 1. The indigenous microbial community at the start of the Warburg respirometry experiments was approximately $8.5 \times 10^7$ cells/g soil, as determined by heterotrophic plate count (R2A agar—9 day). The applied P. paucimobilis concentration, calculated from plate counts (R2A agar) on the inoculum culture, was approximately $7.7 \times 10^6$ cells/g soil.

The indigenous soil microbial community and P. paucimobilis were screened for sensitivity to six different antibiotics on agar plates amended with 2.0% HPC or noble agar plates containing 1.0% IGP medium. The indigenous organisms were applied to the agar plates by spread plating 0.1 ml of a mixture consisting of 1.0 g of soil shaken in 99 ml of dilution water. P. paucimobilis was grown in 1.0% IGP medium in 10 ml culture tubes on a rotary mixer before spread plating. Antibiotic impregnated discs (BBL Sensi-Disc Antibiotic Susceptibility Test Discs, Becton Dickinson, Cockeysville, Md.) were applied to the agar plates. Each disc contained tetracycline (30 mcg), kanamycin (30 mcg), novobiocin (30 mcg), chloramphenicol (30 mcg), streptomycin (10 mcg), and ampicillin (10 mcg). For the indigenous organisms, the sizes of the general zones of inhibition, and a semi-quantitative measure of the number of exceptional colonies within these zones, were determined. For P. paucimobilis, the zones of inhibition were clearly delineated. The most effective antibiotic against P. paucimobilis and the indigenous microorganisms was tetracycline. Tetracyline resistance therefore was selected as a model for other genetic alterations of microorganisms, such as genes conferring PCB degradative enzymes, since the resistant trait is a good marker, and provides no adaptive advantage in soil in the absence of tetracycline.

P. paucimobilis was transformed with the plasmid pRK 293, conferring tetracycline and kanamycin resistance, by triparented mating with Escherichia coli strains harboring the broad-host-range plasmid cloning vectors pRK 293 and the helper plasmid pRK 2013. These pRK plasmids are publicly available and are described by Figurski, D. H., Helinski, D., Proc. Nat. Acad. Sci., 76, 1648–1652, 1979; Ditta et al., Proc. Nat. Acad. Sci., 77, 7347–7351, 1980; Frye et al., Gene, 24, 299–308, 1983; and Ditta et al., Plasmid, 13, 149–153 (1985), which are incorporated herein by reference. Stable transformants were selected by enrichment through three serial cultures in 1.0% IGP medium containing 20 ug/ml tetracycline. Individual transformants were isolated on noble agar plates containing the same media. P. paucimobilis also was successfully transformed with the known plasmid pRK 415 using the same methods.

Plasmid (pRK 293) stability was determined by culturing the transformed microorganism in the presence or absence of tetracycline selection. P. paucimobilis containing pRK 293 (1IGP4-TP) was grown on 1.0% IGP medium containing 20 ug/ml tetracycline. This culture was centrifuged and washed twice with dilution water before inoculation of 0.1 ml into 4 ml of 1.0% IGP medium. The percentages of tetracycline resistant cells in the inoculum and subsequent cultures were determined by performing plate counts on 1.0% IGP agar, and blotting from these plates onto 1.0% IGP agar containing 20 ug/ml tetracycline.

Soil samples (100 g) were prepared with 1.0% HPC, 1.0% IGP, or no substrate amendment according to the methods used for Warburg respirometry. Tetracycline resistant P. paucimobilis (pRK 293) was cultured in 1.0% IGP medium containing 20 ug/ml tetracycline. This culture was centrifuged and washed twice with dilution water before inoculation into the soil samples. The applied inoculum concentration was approximately $3.1 \times 10^6$ viable cells/g soil, as calculated based on plate counts of the inoculum culture on agar containing 1.0% IGP medium and 20 ug/ml tetracycline. The inoculated soil samples were incubated at room temperature. The samples were continuously ventilated at approximately 100 ml/minute/sample with humidified air. Once per day the soil samples were mixed.

For all three soils, plate counts were performed initially, and then bi-weekly, for a period of four weeks. Soil dilutions were prepared for plate counts by adding duplicate 1 g soil subsamples from each flask to 99 ml of dilution water and mixing. Serial dilutions were prepared, and 0.1 ml samples then were spread on three types of agar plates. Total heterotrophs were determined by plating on R2A agar (2 day incubation). The P. paucimobilis population was monitored on noble agar containing 1.0% IGP medium (4 day incubation). The P. paucimobilis population maintaining the tetracycline resistance plasmid (pRK 293) was enumerated by counting all colonies that developed on noble agar containing 1.0% IGP medium and 20 ug/ml tetracycline (4 day incubation).

The growth rate of P. paucimobilis (originally enriched for and isolated on 1.0% IGP) was compared in 4 ml of PAS medium amended with the following filter-sterilized detergents; 1.0% IGP, 0.2% IGP, 0.2% TNX (Triton-X-100, Fisher Scientific, Pittsburgh, Pa.) or 0.2% MAK (Makon 12, Nonyl phenol ethoxylate, Stepan Co., Northfield, Ill.). Each medium was inoculated with P. paucimobilis from a 1.0% IGP agar slant. All cultures were grown to an absorbance of 0.5 at 660 nm before inoculation of 0.1 ml into the same medium for the determination of growth rate. Growth was measured as the increase in absorbance at 660 nm.

The growth curves for P. paucimobilis in 1.0% HPC medium and 1.0% IGP medium are compared in FIG. 7. After approximately 12 hours the 1.0% HPC culture reached an absorbance of 1.0. For the same organism in the detergent based media, 30 hours were required to achieve the same absorbance.

The Warburg respirometry results of P. paucimobilis inoculated soil amended with 1.0% IGP or 1.0% HPC are shown in FIG. 8. The rate of consumption in soil amended with 1.0% HPC, and inoculated with P. paucimobilis, was essentially the same as that of the soil inoculated with autoclaved P. paucimobilis containing only the indigenous populations (FIG. 8B). For the soils amended with 1.0% IGP, consumption was faster and more extensive in the inoculated soil (FIG. 8C).

A comparison of the respirometry curves for the P. paucimobilis inoculated soil amended with 1.0% IGP (FIG. 8C) and the control soils with no substrate amendment (FIG. 8A) indicate that 35–40% of the applied detergent was consumed. Minimal consumption was observed in the detergent amended soil by the indigenous microbial community. For the soils amended with 1.0% HPC (FIG. 8B), 35–40% of the added substrate was consumed in the soils inoculated with either the live or autoclaved P. paucimobilis culture.

Plasmid stability of pRK 293 transformed P. paucimobilis is listed in Table III. After an increase in cell numbers from approximately $1.9 \times 10^6$ to approximately $1.8 \times 10^9$ (approximately 10 divisions), the percentage of tetracycline cells decreased from 96 to 40.

TABLE III

Plasmid pRK 293 stability in P. paucimobilis in the absence of tetracycline selection in 1.0% IGP medium. Total cell concentration and percentage of tetracycline resistant cells were determined at the time of each serial transfer.

|  | CONCENTRATION (C.F.U./ml) | PERCENT TETRACYCLINE RESISTANT |
|---|---|---|
| Tube 1 Initial [a] | $1.9 \times 10^6$ | 96 |
| Final | $1.8 \times 10^9$ | 40 |
| Tube 2 Initial [b] | $4.6 \times 10^7$ | 40 |
| Final | $1.6 \times 10^9$ | 29 |
| Tube 3 Initial [c] | $4.0 \times 10^7$ | 29 |
| Final | $2.2 \times 10^9$ | 12 |

[a] Inoculated with 0.1 ml of a P. paucimobilis culture grown in 1.0% IGP medium with 20 ug/ml tetracycline. Cells were centrifuged and washed twice with dilution water before inculation into Tube 1.
[b] Inoculated with 0.1 ml from Tube 1.
[c] Inoculated with 0.1 ml from Tube 2.

The plate counts in soil unamended or amended with detergent (1.0% IGP) or 1.0% HPC, and inoculated with transformed P. paucimobilis (pRK 293), are shown in FIG. 9. In the absence of soil supplementation (FIG. 9A), total heterotrophic counts remained nearly constant or increased slightly, while the IGP consumers decreased slightly. Virtually all of the added cells retained their tetracycline resistance. Upon supplementation with HPC (FIG. 9B), total heterotrophs increased by more than 1000-fold while the IGP consumers increased slightly then decreased dramatically. FIG. 9C shows the increase in heterotrophs for soil supplemented with the detergent IGP. In this case, IGP consumers increased by almost 1000-fold, accounting for virtually all of the increase in total heterotrophs. Although a significant percentage of these cells lost their tetracycline resistance (pRK 293), the overall increase in tetracycline resistant cells in the soil was considerable.

The growth curves for P. paucimobilis in PAS medium amended with 1.0% IGP, 0.2% IGP, 0.2% TNX, or 0.2% MAK are shown in FIG. 10. P. paucimobilis, originally enriched for and isolated on 1.0% IGP, grew at a comparable rate at lower detergent concentrations (0.2% vs 1.0%) and on the structurally similar detergents TNX and MAK.

EXAMPLE 18

PCB Degradative Recombinant P. paucimobilis/ 1.0% IGP Field Application Vector

Pseudomonas paucimobilis strain 1IGP4 was isolated from enrichment culture on 1.0% IGP which it utilizes as a selective substrate. Polychlorinated biphenyl-degrading genes were obtained from PCB degrading pseudomonads as described by Bedard et al., Appl. Environ. Microbiol., 51:761–768 (1986). These genes were initally cloned in E. coli according to the procedure of Mondello, supra., and subcloned into the plasmid pRK415 suitable for transformation of 1IGP4. Alternatively, plasmids pRK293 or other suitable broad host range or narrow host range cloning vectors can be used. Strain 1IGP4 is transformed with the recombinant PCB degradative plasmid by triparental mating with an E. coli containing the helper plasmid pRK2013 and the E. coli containing the above PCB plasmid.

Transformants are enriched for on PAS medium containing 1.0% IGP and tetracycline (plasmids pRK293 and pRK415 contain tetracycline resistance genes). Suitable transformants are identified by plating and incubating at 25° C. on PAS medium with 1.0% IGP, followed by spraying with 2,3-dihydroxybiphenyl. Yellow colonies are selected, streaked, and isolates are grown in pure culture.

Use of the field application vector is performed by adding either in situ or in a reactor, either by spraying or other known means, IGP and the 1IGP4-PCB recombinant strain to a PCB contaminated soil which has been supplemented with nitrogen and phosphorus, and limed to adjust pH.

EXAMPLE 19

Biological Pesticides

The methods according to the above Examples can be used for producing field application vectors which produce compounds that possess effective pesticidal properties.

For example, Bacillus thuringiensis (Bt) delta-endotoxin is an effective microbial pesticide. Using the factors reported by Watrud et al., supra., potential microbial recipients of the gene encoding the Bt toxin are located. The enrichment culture and isolation techniques according to the above examples are used to isolate micooorganisms in various potential selective substrates. The strains capable of using a particular selective substrate as a sole carbon and energy source are isolated and grown in pure culture.

Using the methods described by Watrud, the isolated strains are transformed with the DNA encoding the Bt toxin and grown in culture. The resulting field application vectors can be introduced into the agricultural domain using known methods.

Deposits

The materials listed below were deposited with the Agricultural Research Service Culture Collection, National Center for Agricultural Utilization Research, US Department of Agriculture, Peoria Ill., USA (NRRL). The deposits were made under the provisions of the Budapest Treaty on the International Recognition of the Deposit of Microorganisms for the Purposes of Patent Procedure and the Regulations thereunder (Budapest Treaty). Maintenance of a viable culture is assured for 30 years from the date of deposit. The organism will be made available by NRRL under the terms of the Budapest Treaty, and subject to an agreement between Applicants and the NRRL which assures unrestricted availability upon issuance of the pertinent U.S. patent. Availability of the desposited strain is not to be construed as a license to practice the invention in contravention of the rights granted under the authority of any government in accordance with its patent laws. The deposit of material does not constitute an admission that the written description contained herein is inadequate to enable the practice of any aspect of the invention, including the best mode, nor is the deposit to be construed as limiting the scope of the claims to the specific illustrations that they represent.

| Microorganism | Deposit Date | NRRL# |
|---|---|---|
| *Pseudomonas paucimobilis* strain 1IGP4-TP | February 27, 1991 | |

What is claimed is:

1. The method of microbiologically degrading organic material in a mixed microbiologically competitive environment which comprises introducing to said environment a recombinantly modified microorganism in the presence of at least one substance not normally utilized by microorganisms indigenous to said environment but utilized as a growth substrate by said recombinantly modified microorganism, said recombinantly modified microorganism having been genetically modified to express upon utilization of said growth substrate at least one enzyme operable in the degradation of said organic material.

2. The method according to claim 1 wherein the DNA of the transformed recombinant microorganism further includes a promoter sequence regulated by the substrate, said promoter sequence being located upstream of the gene encoding said enzyme so as to cause the expression of the enzyme.

3. The method according to claim 1 wherein said substrate is a surfactant.

* * * * *